US012471956B2

(12) United States Patent
Zhu et al.

(10) Patent No.: US 12,471,956 B2
(45) Date of Patent: Nov. 18, 2025

(54) ELASTIC TRACTION SYSTEM

(71) Applicant: BEIJING ROSSUM ROBOT TECHNOLOGY CO., LTD, Beijing (CN)

(72) Inventors: Gang Zhu, Beijing (CN); Ke Xu, Beijing (CN); Xingzhong An, Beijing (CN); Chuan Bai, Beijing (CN); Kewen Mu, Beijing (CN); Wei Tian, Beijing (CN)

(73) Assignee: BEIJING ROSSUM ROBOT TECHNOLOGY CO., LTD, Beijing (CN)

( * ) Notice: Subject to any disclaimer, the term of this patent is extended or adjusted under 35 U.S.C. 154(b) by 0 days.

(21) Appl. No.: 18/558,003

(22) PCT Filed: May 5, 2022

(86) PCT No.: PCT/CN2022/090967

§ 371 (c)(1),
(2) Date: Oct. 30, 2023

(87) PCT Pub. No.: WO2023/173558

PCT Pub. Date: Sep. 21, 2023

(65) Prior Publication Data

US 2024/0245433 A1 Jul. 25, 2024

(30) Foreign Application Priority Data

Mar. 16, 2022 (CN) ......................... 202210256332.0

(51) Int. Cl.
*A61B 17/64* (2006.01)
*A61B 17/00* (2006.01)

(52) U.S. Cl.
CPC ............................... *A61B 17/6408* (2013.01); *A61B 2017/00017* (2013.01); *A61B 2017/00398* (2013.01);
(Continued)

(58) Field of Classification Search
CPC ...... A61H 1/0222; A61H 1/0229; A61H 1/00; A61H 1/02; A61H 1/0218; A61H 1/0292;
(Continued)

(56) References Cited

U.S. PATENT DOCUMENTS 2,221,962 A * 11/1940 Bergfors .............. A61H 1/0214
601/36
2,623,518 A * 12/1952 Vaquette .............. A61H 1/0222
606/242
(Continued)

FOREIGN PATENT DOCUMENTS

CN 109330804 A 2/2019
CN 109730823 A 5/2019
(Continued)

OTHER PUBLICATIONS

CN 215131091U Machine Translation (Year: 2021).*
CN 211067259 Machine Translation (Year: 2020).*

*Primary Examiner* — Kari K Rodriquez
(74) *Attorney, Agent, or Firm* — FisherBroyles, LLP; Roger L. Browdy; Ronni S. Jillions

(57) ABSTRACT

An elastic traction system, including a driving mechanism to provide traction power, a connecting rod connected to an output shaft of the driving mechanism and rotating along with the output shaft, a traction wheel arranged at an end of the connecting rod for rotating along with the connecting rod, a traction wire connected to the traction wheel, and an elastic traction bow connected to the traction wire. An elastic body is arranged at a front end of the traction wire to be connected to various traction tools, the other end of the traction wire is wound around the traction wheel, and the traction wheel is driven by the traction system to rotate, so as to complete a traction operation. The elastic traction bow implements elastic traction of a fracture reduction surgery, provides an elastic activity space for a surgical operation,
(Continued)

and greatly facilitates carrying out various reduction operations during traction.

8 Claims, 9 Drawing Sheets

(52) U.S. Cl.
CPC ............... *A61B 2017/00407* (2013.01); *A61B 2017/00862* (2013.01)

(58) Field of Classification Search
CPC .. A61H 1/0296; A61B 17/6408; A61B 17/66; A61B 17/663; A61B 17/666; A61F 5/3769; A61F 5/3792; A61F 5/04; A61F 5/042; A61F 5/05841; A61F 5/05883
See application file for complete search history.

(56) References Cited

U.S. PATENT DOCUMENTS

| | | | | | |
|---|---|---|---|---|---|
| 2,693,796 | A * | 11/1954 | Warner | A61H 1/0222 | D24/183 |
| 2,861,565 | A * | 11/1958 | Lapierre | A61H 1/0222 | 606/243 |
| 2,907,324 | A * | 10/1959 | Catanzaro | A61H 1/0222 | 602/34 |
| 2,940,441 | A * | 6/1960 | Demarest | A61H 1/0218 | 602/32 |
| 3,894,534 | A * | 7/1975 | Graves | A61H 1/02 | 601/25 |
| 4,356,816 | A * | 11/1982 | Granberg | A61H 1/0222 | 606/241 |
| 4,895,328 | A * | 1/1990 | Ryan | A61H 1/0229 | 248/328 |
| 5,094,445 | A * | 3/1992 | Winkelvoss | A61H 1/0229 | 482/142 |
| 5,273,502 | A * | 12/1993 | Kelsey | A61H 1/0229 | 482/69 |
| 5,478,307 | A * | 12/1995 | Wang | A61H 1/0222 | 606/245 |
| 10,973,673 | B1 | 4/2021 | Skraber | | |
| 2004/0002410 | A1* | 1/2004 | Steinbach | A63B 21/1672 | 482/121 |
| 2009/0227929 | A1* | 9/2009 | Gondringer | A61F 5/04 | 602/33 |

FOREIGN PATENT DOCUMENTS

| | | | |
|---|---|---|---|
| CN | 110327105 | A | 10/2019 |
| CN | 211067259 | U | 7/2020 |
| CN | 211521163 | U | 9/2020 |
| CN | 212066836 | U | 12/2020 |
| CN | 215131091 | U | 12/2021 |
| CN | 215739736 | U | 2/2022 |

* cited by examiner

ELASTIC TRACTION SYSTEM

TECHNICAL FIELD

The present disclosure belongs to the technical field of medical instruments, in particular to an elastic traction system for a fracture reduction surgery.

BACKGROUND

In orthopedic diseases, doctors often carry out traction to treat various diseases. An orthopedic lower limb traction system, also known as an orthopedic traction frame, is a basic device in an orthopedic operating room. It can be connected to an operating table to support the body of a patient during an orthopedic lower limb traction surgery and perform traction reduction on the affected lower limb. However, the conventional orthopedic lower limb traction system has a complex structure, takes up a large space around the operating table, and is inconvenient for medical personnel to perform surgical operations. In addition, the intraoperative photography of a traction reduction site by a C-shaped arm is easily affected during traction. At present, most orthopedic traction frames are manual traction frames, which are inconvenient to operate.

Moreover, existing traction bows are all basically rigid traction bows. A traction wire is directly connected to a traction bow, and a traction mechanism pulls the traction bow by the traction wire, so as to pull the distal end of a fracture. However, in some fracture reduction surgeries, rigid traction is inconvenient for doctors to perform reduction operations. For example, during a pelvic fracture reduction surgery, after the fractured lower limb of a patient is pulled to a certain position, the fractured end of the pelvis needs to gradually move towards the healthy side of the pelvis until a closed position is reached. In this case, an existing traction bow cannot well meet the surgical operation requirements. Furthermore, the existing traction bow has a single function and poor flexibility, cannot be quickly adjusted in tension, and is inconvenient to operate.

Therefore, a novel elastic traction system needs to be designed in the art, so as to facilitate the implementation of various reduction surgery operations during the traction.

SUMMARY

To solve the above technical problems, the present disclosure provides an elastic traction system, including:

- a driving mechanism, configured to provide traction power;
- a connecting rod, connected to an output shaft of the driving mechanism and rotating along with the output shaft;
- a traction wheel, arranged at an end of the connecting rod and capable of rotating along with the connecting rod, where a traction wire is connected to the traction wheel; and
- an elastic traction bow, connected to the traction wire.

Further, the elastic traction bow includes:

- an elastic body, having one end connected to the traction wire; and
- a tensional traction bow, having one end connected to the other end of the elastic body.

Further, the elastic body includes an outer barrel and an elastic element, where a moving portion is arranged at one end of the outer barrel and connected to the traction wire, a connecting portion is arranged at the other end of the outer barrel, and the tensional traction bow is connected to the connecting portion; and

- the elastic element is arranged in the outer barrel and has one end fixedly connected to the connecting portion and the other end fixedly connected to the moving portion.

Further, an inner barrel is further included and arranged in the outer barrel, where one end of the inner barrel is connected to the moving portion, and the elastic element is arranged in the inner barrel.

Further, a connecting rod is further included and detachably connected between the elastic body and the traction bow, where an annular clamping groove is arranged at one end of the connecting rod.

Further, the connecting portion includes:

- an interface inner barrel, uniformly provided with a plurality of through holes along an outer circumference;
- an interface outer barrel, slidably sleeved outside the interface inner barrel; and
- a plurality of steel balls, arranged between the interface inner barrel and the interface outer barrel, and partially entering the through holes.

When the interface outer barrel slides relative to the interface inner barrel, the steel balls extend into the interface inner barrel or exit from the interface inner barrel.

Further, a locking mechanism is further included and arranged outside the interface outer barrel and configured to lock the interface outer barrel.

Further, the moving portion includes:

- a clamping groove, configured to be connected to the traction wire; and
- a turnover cover, openably assembled on the moving portion, where the turnover cover is opened to expose the clamping groove, and a wire groove is formed between the turnover cover and a moving portion body.

Further, the tensional traction bow includes:

- a pair of bow arms arranged symmetrically, where a connecting portion connected to a bone needle is arranged at an end of each of the bow arms;
- a connecting arm, rotatably connected to a front end of each of the bow arms;
- a pair of tension arms, symmetrically arranged at positions, close to the front ends, of the bow arms, where one end of each of the tension arms is rotatably connected to a corresponding one of the bow arms; and
- an adjustment mechanism, having two ends movably connected to the other ends of the pair of tension arms, respectively, and configured to adjust forward or backward movement of the pair of tension arms.

Further, the adjustment mechanism includes:

- a ratchet shaft, externally provided with ratchet teeth, having two ends movably connected to the other ends of the pair of tension arms, respectively, and connected to the connecting arm by a shaft sleeve; and
- a ratchet wrench, movably connected to the ratchet shaft by a shaft sleeve and provided with a pawl, where the pawl can be engaged with the ratchet teeth of the ratchet shaft.

Further, the pawl includes a first pawl tooth and a second pawl tooth. The first or second pawl tooth is engaged with the ratchet teeth by rotating the pawl, and the ratchet wrench can be turned to implement counterclockwise or clockwise unidirectional rotation of the ratchet shaft.

Further, a pair of connecting pieces are further included, and have one ends movably connected to the other ends of the pair of tension arms by rotary shafts, and the other ends provided with internal threaded holes or external threaded rods, where the two connecting pieces have opposite thread directions; and an external threaded rod or an internal threaded hole is arranged at an end of the ratchet shaft, two ends of the ratchet shaft have opposite thread directions, and the external threaded rod or the internal threaded hole is in threaded connection with a corresponding one of the internal threaded holes or a corresponding one of the external threaded rods, respectively.

Further, the ratchet teeth are arranged in a middle of the ratchet shaft; and the ratchet wrench is movably connected to the ratchet shaft by two wrench shaft sleeves, the ratchet teeth are located between the two wrench shaft sleeves, and the pawl is arranged in a middle of the ratchet wrench and corresponds to the ratchet teeth.

Further, the ratchet wrench further includes:

a pawl rotating shaft, on which the pawl is rotatably arranged; and an ejector block, arranged in a spring cavity of the ratchet wrench, where an outer end of the ejector block is against a back of the pawl to limit the pawl, and a spring is arranged at the other end of the ejector block.

Further, the connecting portion includes:

a clamp base, arranged on the bow arms;

a clamp upper seat, correspondingly arranged on the clamp base; and a knob and a lead screw, where the knob is arranged at one end of the lead screw, and the lead screw passes through the clamp upper seat and is connected to the clamp base.

Further, a needle groove is arranged on the clamp base and/or the clamp upper seat.

Further, the needle groove is arranged on a front side of the lead screw.

Further, the clamp base is movably arranged on the bow arms.

Further, the traction system includes a keeping portion configured to keep the traction system in a stable state. The keeping portion may include a connecting apparatus and/or a support apparatus.

Further, the driving mechanism includes a worm gear mechanism, where one end of a worm screw is connected to a handle, and a shaft center of a worm wheel is connected to the output shaft.

Further, the traction system further includes:

a base, a bracket, and telescopic rods, where the telescopic rods are telescopically connected between the base and the bracket; and a telescopic shaft, telescopically connected between the output shaft and the connecting rod.

Further, the driving mechanism is arranged on the base, the base is provided with two telescopic support legs, and a table clamp is arranged at an upper end of the bracket.

Further, an annular sleeve is arranged on the bracket, and an end of the telescopic shaft and the connecting rod are clamped in the annular sleeve.

Further, the connecting rod may include a plurality of portions connected in series.

Further, the traction wheel includes:

a traction wheel body, having a penetrative circular through hole in a middle;

a wire groove, arranged on an outer circumference of the traction wheel body;

a rotary clamping portion, configured to rotatably clamp the traction wheel to the connecting rod; and a fixed clamping portion, configured to non-rotatably clamp the traction wheel to the connecting rod.

Further, the rotary clamping portion includes a plurality of elastic joints uniformly distributed around the circular through hole, and the elastic joints are capable of retractably extending into the circular through hole.

Further, the rotary clamping portion includes:

a plurality of spring cavities, uniformly distributed around the circular through hole and communicating with the circular through hole through the traction wheel body;

a plurality of springs, arranged in the plurality of spring cavities, respectively;

a plurality of elastic joints, arranged in the plurality of spring cavities, respectively, where each of the elastic joints has one end extending into the circular through hole and the other end abutting against a corresponding one of the springs; and a plurality of sealing covers, arranged on the traction wheel body and configured to seal the spring cavities.

Further, the fixed clamping portion is a clamping groove arranged at a bottom of the traction wheel body.

Further, the traction wheel further includes:

a rotating ring, rotatably arranged on the traction wheel body and coaxial with the circular through hole; and a baffle, connected to the rotating ring and located on an outer side of the wire groove.

Further, the traction wheel further includes a wire clamping groove elastically arranged on the traction wheel body and configured to clamp the traction wire between a side surface of the traction wheel body and the wire clamping groove.

Further, a head of each of the elastic joints is hemispherical.

Further, the traction wheel body is cylindrical in shape.

Further, the wire groove is an annular groove.

Further, a traction wire fixing portion is provided in the wire groove.

Further, the driving mechanism includes a motor and a speed reducer, where an output shaft of the motor is connected to the connecting rod by the speed reducer.

Further, a control unit and a torsion tester are further included, where the torsion tester is connected between the speed reducer and the connecting rod by a coupling, and the control unit is electrically connected to the torsion tester and the motor.

Further, two or more support legs are further included, where the support legs are electric push rods electrically connected to the control unit.

The elastic traction system according to the present disclosure has a simple structure, the elastic body can be arranged at a front end of the traction wire to be connected to various traction tools, the other end of the traction wire is wound around the traction wheel, and the traction wheel is driven by the traction system to rotate, so as to complete a traction operation.

The elastic traction system according to the present disclosure may be manually or electrically driven. When the motor is used for driving, the operation is simple, convenient and labor-saving; and the torsion tester can be arranged to accurately control a tractive force, which improves the safety of the traction operation.

In addition, through the arrangement of electric support legs or telescopic rods, a height of the bracket can be adjusted to adapt to different heights of operating tables.

The traction wheel in the present disclosure can achieve two connection states on the connecting rod through the arrangement of the rotary clamping portion and the fixed clamping portion, and the two connection states can be freely switched. When the traction wheel is rotatably clamped, the traction wheel can rotate on the connecting rod, making it convenient for wire pay-off and take-up. When the traction wheel is fixedly clamped, the traction wheel is clamped to the connecting rod, and is not rotatable relative to the connecting rod but can rotate along with the connecting rod. In this case, the traction wheel can be used to carry out traction.

The traction wheel in the present disclosure is provided with the baffle, which blocks on the outer side of the wire groove to prevent the traction wire from being ejected out of the wire groove. The traction wheel is further provided with the wire clamping groove, which is configured to clamp the end of the traction wire after wire take-up so as to prevent the traction wire from being payed off.

By adding the elastic body, the elastic traction bow in the present disclosure implements elastic traction of a fracture reduction surgery, provides an elastic activity space for a surgical operation, and greatly facilitates a doctor to carry out various reduction operations during traction.

In addition, the elastic body and the traction bow in the present disclosure are detachably connected. If the elastic body does not need to be used, the traction wire can be directly connected to the traction bow, which provides the doctor with more ways to use instruments. A fast interface is provided between the elastic body and the traction bow, which facilitates mounting and dismounting; and a locking structure is provided, which achieves safety and reliability after connection.

The traction bow in the present disclosure is the tensional traction bow. Through the arrangement of the adjustment mechanism, the tension arms can be conveniently adjusted, so as to adjust a tension of the traction bow. With the ratchet wrench capable of being turned bidirectionally, the tension of the traction bow can be conveniently adjusted, and especially during the traction, the tension can be arbitrarily adjusted. Through the arrangement of the clamp base and the clamp upper seat, the bone needle can be conveniently clamped, which can ensure that the bone needle is not loosened under the condition of an increase in tension.

In addition to the technical problems solved by the present disclosure, the technical features of the formed technical solutions, and the advantages brought by the technical features of these technical solutions described above, other technical features of the present disclosure and the advantages brought by these technical features will be further described in conjunction with the accompanying drawings.

REFERENCE SIGNS

Figure 1:
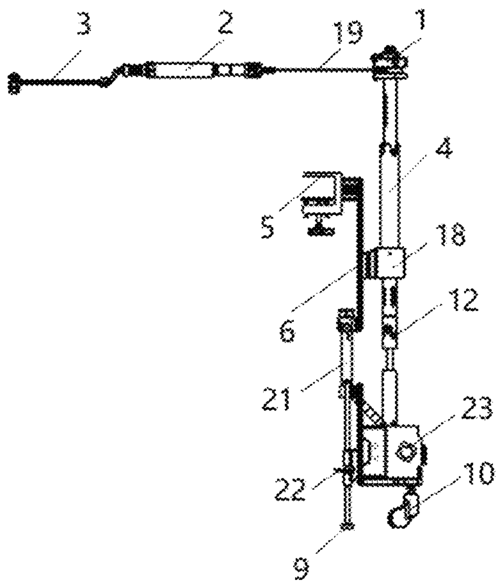
FIG. 1 is a schematic structural diagram of a manual traction system according to a first embodiment of the present disclosure.

1 traction wheel, 2 elastic body, 3 traction bow, 4 connecting rod, 5 table clamp, 6 bracket, 7 coupling, 8 torsion tester, 9 support leg, 10 universal wheel, 11 motor, 12 coupling, 13 speed reducer, 14 base, 15 control unit, 16 signal line, 17 transmission shaft, 18 annular sleeve, 19 traction wire, 20 connecting arm, 21 telescopic rod, 22 support leg knob, 23 worm screw, 24 worm wheel, 25 telescopic shaft, 26 handle, and 27 output shaft;

101 through hole, 102 elastic joint, 103 wire groove, 104 cross clamping groove, 105 baffle, 106 wire clamping groove, 107 sealing cover, 108 spring cavity, and 109 rotating ring;

201 outer barrel, 202 inner barrel, 203 moving portion, 204 spring, 205 connecting ring, 206 spring hanging point, 207 locking sleeve, 208 interface spring, 209 interface inner barrel, 210 inclined portion, 211 steel ball, 212 spring hanging point, 213 interface outer barrel, 214 clamping groove, 215 turnover cover, 216 wire groove, 217 locking hole, 218 connector, 219 annular clamping groove, and 220 connecting hole;

300 ratchet wrench, 301 bow arm, 302 clamp base, 303 clamp upper seat, 304 knob, 305 lead screw, 306 tension arm, 307 connecting arm, 308 shaft sleeve, 309 sealing cap, 310 spring, 311 ejector block, 312 pawl, 313 pawl rotating shaft, 314 ratchet teeth, 315A first pawl tooth, 315B second pawl tooth, 316 connecting piece, 317 ratchet shaft, 318 spring cavity, 319 first position, and 320 second position;

401 first annular groove, 402 second annular groove, and 403 cross tenon.

DETAILED DESCRIPTION OF THE EMBODIMENTS

In the description of the present disclosure, it should be noted that, unless otherwise explicitly specified and defined, the terms "mounting", "connecting", and "connection" should be understood in a broad sense, for example, they may be a fixed connection, a detachable connection, or an integrated connection; and may be a direct connection, or an indirect connection via an intermediate medium, or communication inside two elements. Those of ordinary skill in the art may understand the specific meanings of the above terms in the present disclosure according to the specific circumstances.

In addition, in the description of the present disclosure, "a plurality of" and "a plurality of groups" mean two or more, and "several" and "several groups" mean one or more, unless otherwise stated.

The present disclosure provides an elastic traction system, including: a driving mechanism, configured to provide traction power; a connecting rod, connected to an output shaft of the driving mechanism and rotating along with the output shaft; a traction wheel, arranged at an end of the connecting rod and capable of rotating along with the connecting rod, where a traction wire is connected to the traction wheel; and an elastic traction bow, connected to the traction wire.

The elastic traction bow in the present disclosure may include: an elastic body, having one end connected to the traction wire; and a traction bow, having one end connected to the other end of the elastic body. By adding the elastic body between the traction wire and the traction bow, elastic traction of a fracture reduction surgery is implemented, an elastic activity space is provided for a surgical operation, and a doctor is greatly facilitated to carry out various reduction operations during traction.

Preferably, the elastic body includes an outer barrel and an elastic element, where a moving portion is arranged at one end of the outer barrel and connected to the traction wire, a connecting portion is arranged at the other end of the outer barrel, the traction bow is connected to the connecting portion, and the elastic element is arranged in the outer barrel and has one end fixedly connected to the connecting portion and the other end fixedly connected to the moving portion. The elastic element is connected between the moving portion and the connecting portion, the moving portion needs to overcome an elastic force of the elastic element when moving relative to the outer barrel, and the elastic force of the elastic element can be selected according to the surgical requirements.

Preferably, an inner barrel is further included and arranged in the outer barrel, where one end of the inner barrel is connected to the moving portion, and the elastic element is arranged in the inner barrel. When the moving portion moves away from the outer barrel under the action of a tractive force, the inner barrel moves along with the moving portion, and part of the inner barrel extends out of the outer barrel without exposing the elastic element.

Preferably, the connecting portion is a fast interface, including: an interface inner barrel, uniformly provided with a plurality of through holes along an outer circumference; an interface outer barrel, slidably sleeved outside the interface inner barrel; and a plurality of steel balls, arranged between the interface inner barrel and the interface outer barrel, and partially entering the through holes. When the interface outer barrel slides relative to the interface inner barrel, the steel balls extend into the interface inner barrel or exit from the interface inner barrel.

Specifically, an inner wall of the interface outer barrel is provided with an inclined portion and a parallel portion relative to an outer wall of the interface inner barrel. A rear of the interface outer barrel is provided with an interface spring, which provides a pre-thrust for the interface outer barrel, so that the interface outer barrel is located in a locking position, and an end of the interface outer barrel extends out of an end of the interface inner barrel. In this case, the steel balls are located between the through holes of the interface inner barrel and the inclined portion of the interface outer barrel, and the steel balls are squeezed by the inclined portion to partially extend into the interface inner barrel. When sliding relative to the interface inner barrel, the interface outer barrel moves to an unlocking position against an elastic force of the interface spring. In this case, the end of the interface outer barrel is flush with the end of the interface inner barrel, and the inclined portion does not squeeze the steel balls any more. The steel balls are located between the parallel portion and the through holes, and parts, extending into the interface inner barrel, of the steel balls are retractable. When released, the interface outer barrel returns to the locking position under the elastic force of the interface spring.

An annular clamping groove is arranged at one end of the connecting rod. When the connecting rod is inserted, an end of the annular clamping groove is inserted into the interface inner barrel. The annular clamping groove corresponds in position to the through holes of the interface inner barrel. The steel balls extending into the interface inner barrel are clamped in the annular clamping groove. Specifically, when the connecting rod needs to be mounted, the interface outer barrel is pushed to the unlocking position. In this case, the steel balls retract from the through holes of the interface inner barrel, and an insertion end of the connecting rod can be inserted into the interface inner barrel. When released, the interface outer barrel returns to the locking position under the elastic force of the interface spring. In this case, the steel balls are squeezed by the inclined portion to partially extend into the interface inner barrel to be clamped in the annular clamping groove of the connecting rod, so as to complete the assembly.

More preferably, a locking structure is further included and can lock the interface outer barrel in the locking position to prevent the separation of the connecting rod due to sliding of the interface outer barrel thanks to a misoperation. For example, the locking structure may be a locking sleeve connected to the outer barrel in a threaded manner. After the interface outer barrel returns to the locking position, the locking sleeve can be screwed down. In this case, the interface outer barrel is not slidable.

Preferably, the moving portion may include a turnover cover openably assembled on the moving portion. The turnover cover is opened to expose a clamping groove, and the clamping groove is located in a moving portion body and configured to be connected to the traction wire. For example, a clamping block is mounted at one end of the traction wire and embedded into the clamping groove, so as to complete the connection between the traction wire and the moving portion, with convenient operation. A wire groove is formed between the turnover cover and the moving portion body, and the wire groove communicates with the clamping groove, which facilitates the embedding of the traction wire.

The tensional traction bow includes: a pair of bow arms arranged symmetrically, where a connecting portion connected to a bone needle is arranged at an end of each of the bow arms; a connecting arm, rotatably connected to a front end of each of the bow arms; a pair of tension arms, symmetrically arranged at positions, close to the front ends, of the bow arms, where one end of each of the tension arms is rotatably connected to a corresponding one of the bow arms; and an adjustment mechanism, having two ends movably connected to the other ends of the pair of tension arms, respectively, and configured to adjust forward or backward movement of the pair of tension arms.

The tensional traction bow in the present disclosure adjusts a movement direction of the pair of tension arms by the adjustment mechanism, which can adjust the extension and retraction of the bow arms, so as to adjust a magnitude of the tension.

Preferably, the adjustment mechanism is a ratchet mechanism, including: a ratchet shaft, externally provided with ratchet teeth, having two ends movably connected to the other ends of the pair of tension arms, respectively, and connected to the connecting arm by a shaft sleeve; and a ratchet wrench, movably connected to the ratchet shaft by a shaft sleeve and provided with a pawl, where the pawl can be engaged with the ratchet teeth of the ratchet shaft. Preferably, the pawl includes a first pawl tooth and a second pawl tooth. The first or second pawl tooth is engaged with the ratchet teeth by rotating the pawl, and the ratchet wrench can be turned to implement counterclockwise or clockwise unidirectional rotation of the ratchet shaft.

Preferably, an external threaded rod or an internal threaded hole is arranged at an end of the ratchet shaft, and two ends of the ratchet shaft have opposite thread directions. A movably connected connecting piece is arranged at an end of the tension arm, and the connecting piece is provided with an internal threaded hole or an external threaded rod, which is in threaded connection with the external threaded rod or the internal threaded hole at the end of the ratchet shaft. Therefore, when the ratchet shaft rotates in a direction, the pair of tension arms can be driven to move towards each other; and when the ratchet shaft rotates in an opposite direction, the pair of tension arms can be driven to move away from each other.

Different pawl teeth of the pawl are engaged with the ratchet teeth, and the ratchet shaft can rotate in a predetermined direction by turning the ratchet wrench to drive the tension arms to move to adjust the extension and retraction of the bow arms, so as to adjust the magnitude of the tension.

Preferably, an ejector block is arranged to limit the pawl. The ejector block may be against a first position or a second position on a back of the pawl. When the ejector block is against the first position, the first pawl tooth is engaged with the ratchet teeth, and when the ejector block is against the second position, the second pawl tooth is engaged with the ratchet teeth. Preferably, the ejector block is arranged elastically, so that the ejector block can be easily switched between the first position and the second position by pulling the pawl, and then a rotation direction of the ratchet shaft can be switched, so as to increase or reduce the tension.

Preferably, the connecting portion includes: a clamp base, arranged on the bow arms; a clamp upper seat, correspondingly arranged on the clamp base; and a knob and a lead screw, where the knob is arranged at one end of the lead screw, and the lead screw passes through the clamp upper seat and is connected to the clamp base. The lead screw can be driven by turning the knob to rotate to fasten the clamp upper seat to the clamp base, or the lead screw is rotated reversely to separate the clamp upper seat from the clamp base, making it easy to clamp or dismount the bone needle.

Preferably, a needle groove is arranged on the clamp base and/or the clamp upper seat, which facilitates the fixation of the bone needle, so that the bone needle is less prone to movement during traction.

Preferably, the needle groove is arranged on a front side, namely, one side, close to the traction bow, of the lead screw, so that even if the bone needle separates from the needle groove during the traction, it will be blocked by the lead screw from separating from the traction bow.

Preferably, the clamp base is movably arranged on the bow arms. The clamp base can rotate a certain angle or move a certain distance back and forth, so that when the bone needle is offset or skewed, the clamp base can still be adjusted to allow the bone needle to be placed in the needle groove. The clamp upper seat and the lead screw are assembled on the clamp base and can be adjusted synchronously with the clamp base, thus implementing the alignment and clamping of the clamp base and the clamp upper seat.

Preferably, the traction wheel includes: a traction wheel body, having a penetrative circular through hole in a middle; a wire groove, arranged on an outer circumference of the traction wheel body; a rotary clamping portion, configured to rotatably clamp the traction wheel to the connecting rod; and a fixed clamping portion, configured to non-rotatably clamp the traction wheel to the connecting rod.

The traction wheel in the present disclosure can achieve two connection states on the connecting rod through the arrangement of the rotary clamping portion and the fixed clamping portion, and the two connection states can be freely switched. When the traction wheel is rotatably clamped, the traction wheel can rotate on the connecting rod, making it convenient for wire pay-off and take-up. When the traction wheel is fixedly clamped, the traction wheel is clamped to the connecting rod, and is not rotatable relative to the connecting rod but can rotate along with the connecting rod. In this case, the traction wheel can be used to carry out traction.

The connecting rod is cylindrical and can be matched with the circular through hole of the traction wheel, and the traction wheel is assembled on the connecting rod via the circular through hole. A first annular groove, a second annular groove, and a tenon are arranged at the end of the connecting rod in sequence from top to bottom. When the rotary clamping portion is clamped in the first circular groove of the connecting rod, the traction wheel and the connecting rod are in a rotary connection state, and the traction wheel can rotate about the connecting rod. When the rotary clamping portion is clamped in the second annular groove of the connecting rod, the fixed clamping portion is connected to the tenon. The fixed clamping portion is a clamping groove arranged at a bottom of the traction wheel body. In this case, the traction wheel and the connecting rod are in a fixed connection state, and the traction wheel cannot rotate about the connecting rod.

Preferably, the rotary clamping portion includes a plurality of elastic joints uniformly distributed around the circular through hole, and the elastic joints are capable of retractably extending into the circular through hole. The elastic joints extend into the circular through hole and can be clamped in the first annular groove or the second annular groove. The elastic joints are in an elastic and telescopic state, so that the elastic joints can be switched between the first annular groove and the second annular groove. When the traction wheel is pressed down with a force, the elastic joints retract to separate from the first annular groove. The traction wheel moves down along the connecting rod, and when moving to the second annular groove, the elastic joints elastically extend out to be clamped in the second annular groove. When the traction wheel is pulled up, the elastic joints can separate from the second annular groove. When moving to the first annular groove, the elastic joints elastically extend out to be clamped in the first annular groove.

Preferably, the rotary clamping portion includes a plurality of spring cavities uniformly distributed around the circular through hole and formed by communication between the traction wheel body and the circular through hole in the middle. Springs are mounted in the spring cavities, the elastic joints are arranged at front ends of the springs, back ends of the springs abut against sealing covers, and the sealing covers are mounted on the traction wheel body to seal the spring cavities. Front ends of the elastic joints can penetrate into the circular through hole under an elastic force of the springs, and when a received squeezing force is greater than the elastic force of the springs, the elastic joints can retract into the spring cavities.

Preferably, the traction wheel further includes a rotating ring, and the rotating ring may be arranged on an upper end surface of the traction wheel, may be coaxial with the circular through hole, and is rotatable relative to the traction wheel. A baffle is connected to the rotating ring and located on an outer side of the wire groove. The traction wheel rotates during wire take-up and pay-off. The baffle blocks on the outer side of the wire groove, so that the traction wire can be prevented from being ejected out of the wire groove. The baffle is rotatable relative to the traction wheel by being connected to the rotating ring, so that the baffle will not interfere with the wire take-up and pay-off operations.

Preferably, the traction wheel further includes a wire clamping groove, an open groove can be formed on an upper end surface of the traction wheel body, and one end of the wire clamping groove is open and communicates with the wire groove. The wire clamping groove is configured to clamp the end of the traction wire. More preferably, the wire clamping groove can be elastically assembled with a side surface of the traction wheel. When the wire needs to be clamped, the wire clamping groove is pulled out, the traction wire is placed into the wire clamping groove, then the wire clamping groove is released, and the wire clamping groove will be tightly attached to the side surface of the traction wheel under an elastic pull force, so as to clamp the traction wire. The traction wire and the traction wheel need to be disinfected before the traction operation. In this case, the traction wire is wound in the wire groove of the traction wheel. The traction wire is usually a steel wire rope with great elasticity, so that it is easy to loosen and inconvenient to disinfect. The end of the traction wire is clamped in the wire clamping groove to be fixed, so that the traction wire is neat to take up and convenient to disinfect.

Preferably, a traction wire fixing portion is provided in the wire groove. One end of the traction wire is fixedly connected into the wire groove, the traction wire is wound in the wire groove, and the other end of the traction wire can be connected to the traction bow. The traction wire is payed off from the wire groove during use and is taken up into the wire groove after use.

Preferably, the traction system according to the present disclosure is driven by a motor. The connecting rod is driven by the motor to rotate, and the traction wheel is driven to rotate to tension the traction wire, so as to complete the traction.

Preferably, the driving mechanism includes a motor and a speed reducer, where an output shaft of the motor is connected to the connecting rod by the speed reducer.

To adapt to different heights of operating tables, a height of the traction system according to the present disclosure can be adjusted. Specifically, two or more support legs are included. The support legs are preferably electric push rods electrically connected to the control unit. A length of the electric push rods can be controlled, so that an upper end of a bracket is connected to an operating table by a table clamp. The support legs are supported on the ground to keep the functions of connection and support.

Preferably, the electric traction system further includes a torsion tester connected between the output shaft and the connecting rod by a coupling, and the torsion tester is electrically connected to the control unit. The torsion tester is arranged on a transmission shaft, so that a magnitude of an output torque can be accurately detected to accurately control the tractive force, which improves the safety of traction.

Preferably, the bracket and a base in the present disclosure are connected together, and two or more universal wheels may be further arranged on the base, which facilitates the electric traction system to move. After the traction system moves to a traction position, the universal wheels can be locked.

Preferably, an annular sleeve is arranged on the bracket, and an end of a telescopic shaft and the connecting rod are clamped in the annular sleeve. Preferably, a position of the annular sleeve is lower than a position of the table clamp, and the connecting rod on the annular sleeve is detachable. In other words, in a dismounting state, the table clamp is a highest point of the traction system. This structural design easily meets the disinfection requirements of an operating room. The connecting rod on the annular sleeve, the traction wheel, and the traction wire need to be disinfected, and can be dismounted and disinfected separately before each use. The table clamp of the traction system is connected to an operating table board, and a part under the operating table board does not need to be disinfected. During surgical traction, the table clamp and part of the bracket are covered by a disinfected bed sheet, so as to meet the requirements of a sterile area on a table surface.

More preferably, the connecting rod may include a plurality of portions connected in series. To be applicable to traction operations at different heights, the connecting rod may include a plurality of sections insertably connected in series. A single section of the connecting rod should not be too long, and each section of the connecting rod should be conveniently put into a disinfection container for disinfection.

Preferably, the electric traction system includes a controller that can be electrically connected to the control unit in a wireless or wired manner. The controller includes a display screen and a control button, where the control button may be a mechanical or touch button. The display screen can display a value of the tractive force in real time, where the value of the tractive force can be calculated according to a torque value measured by the torsion tester. A predetermined value of the tractive force can be set by an operation button, and then a start button is clicked. The motor will rotate under the control of the control unit. When the tractive force reaches a preset value, the motor stops rotating. A magnitude of the tractive force can also be adjusted by a button, such as being increased or reduced. The motor will rotate forwards or reversely under the control of the control unit. When the tractive force reaches an adjusted value, the motor stops rotating. The controller is provided with an emergency stop button, which can stop the electric traction system with one key.

Optionally, the driving mechanism may be manually driven. Preferably, the driving mechanism includes a worm gear mechanism, where one end of a worm screw is connected to a handle, and a shaft center of a worm wheel is connected to the output shaft. The worm wheel is matched with the worm screw, the structure is simple and reliable, and the output shaft can rotate by manually rotating the worm screw. Preferably, the worm wheel is connected to the output shaft by a universal coupling. Preferably, the handle and the worm screw can be connected by the ratchet mechanism, where the ratchet mechanism may be bidirectionally adjustable, so that a rotation direction of the worm screw driven by the handle can be conveniently adjusted by adjusting the ratchet mechanism to increase or reduce the tractive force.

Preferably, the traction system further includes: a base, a bracket, and telescopic rods, where the telescopic rods are telescopically connected between the base and the bracket; and a telescopic shaft, telescopically connected between the output shaft and the connecting rod. To adapt to different heights of operating tables, the height of the traction system according to the present disclosure can be adjusted. Specifically, the telescopic rods, preferably two parallel telescopic rods are arranged between the bracket and the base. A length of the telescopic rods is adjusted, so that the upper end of the bracket is connected to the operating table by the table clamp. The base is supported on the ground and then the telescopic rods are locked to keep the functions of connection and support. Correspondingly, the telescopic shaft is arranged at one end of the output shaft, and a length of the telescopic shaft may be adjusted to meet different heights of application scenarios. For example, an outer shaft barrel and an inner shaft barrel may be arranged, and the inner shaft barrel is assembled in the outer shaft barrel, and is not rotatable relative to the outer shaft barrel but can make telescopic movement along an axis. One end of the outer shaft barrel may be connected to the output shaft, while one end of the inner shaft barrel may be connected to the connecting rod, thereby ensuring that a driving force of the output shaft is transmitted to the connecting rod. Preferably, the telescopic shaft is connected to the output shaft by a universal coupling.

Preferably, the driving mechanism is arranged on the base, the base is provided with two telescopic support legs, and the table clamp is arranged at the upper end of the bracket. Two or more universal wheels may be further arranged on the base, which facilitates the traction system to move. After the traction system moves to the traction position, the universal wheels can be locked. Preferably, the support legs can be lowered to be supported on the ground, making the base of the traction system more stable. Preferably, the support legs are of a telescopic structure, and are provided with support leg knobs for locking or releasing the support legs. During use, the support leg knobs are released first, the support legs are adjusted to be stably supported on the ground, and then the support leg knobs are locked to keep a support state of the support legs.

A working process of the traction system according to the present disclosure is as follows:

The traction bow is mounted at a traction site of a patient, the connecting rod is inserted into the annular sleeve, and the traction wheel is rotated and clamped onto the connecting rod. In this case, the traction wheel can rotate about the connecting rod, making it convenient to lead out the traction wire from the traction wheel to connect it to the traction bow. Then, the traction wheel is fixedly clamped onto the connecting rod. In this case, the traction wheel is fixed and not rotatable relative to the connecting rod. The driving mechanism is started and outputs the driving force to the connecting rod, so as to rotate the connecting rod. The traction wheel rotates along with the connecting rod, and the traction wire is wound in the wire groove of the traction wheel, so as to tension the traction wire. The traction operation on the site of the patient is implemented by the traction bow at a front end. After the traction is completed, the driving mechanism is controlled to rotate reversely, and the output shaft drives the connecting rod to rotate reversely, so that the traction wheel rotates reversely, and the traction wire is released from the traction wheel. In this case, the traction wire can be separated from the traction bow. Then, the traction wheel and the connecting rod are rotatably clamped, the traction wheel is rotated to implement the wire take-up operation, and the end of the traction wire is clamped in the wire clamping groove.

To make the objectives, technical solutions and advantages of the embodiments of the present disclosure clearer, the technical solutions in the embodiments of the present disclosure will be clearly and completely described below in conjunction with the accompanying drawings in the embodiments of the present disclosure. Apparently, the described embodiments are some rather than all of the embodiments of the present disclosure. All other embodiments obtained by those of ordinary skill in the art based on the embodiments of the present disclosure without creative efforts shall fall within the scope of protection of the present disclosure.

First Embodiment

Figure 2:
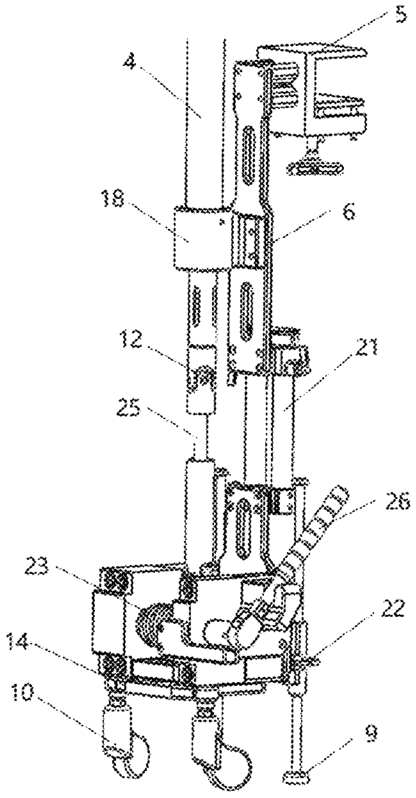
FIG. 2 is a schematic diagram of a partial structure of the manual traction system according to the first embodiment of the present disclosure.
Figure 3:
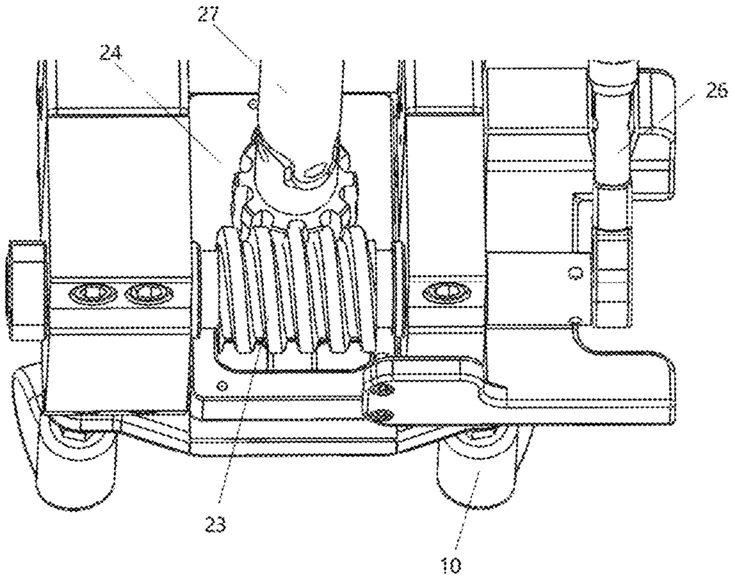
FIG. 3 is a schematic sectional view of a worm gear mechanism in the first embodiment of the present disclosure.

As shown in FIGS. 1-3, a traction system in this embodiment includes a connecting rod 4, where a traction wheel 1 is assembled at an upper end of the connecting rod, and a traction wire 19 is wound around the traction wheel 1. A connecting arm 20 is connected to one end of a traction bow 3 and is configured to be connected to an elastic body 2, and the traction wire 19 is connected to the other end of the elastic body 2. The connecting arm 20 is detachably connected between the traction bow 3 and the elastic body 2. The connecting rod 4 is inserted into an annular sleeve 18. In this embodiment, the connecting rod includes two sections connected in series and inserted into each other.

A table clamp 5 is arranged at an end of a bracket 6, and the annular sleeve 18 is arranged on the bracket 6 and is lower than the table clamp 5 in position. Telescopic rods 21 are arranged between the bracket 6 and a base 14, and two universal wheels 10 and two support legs 9 are arranged on the base 14. The support legs 9 are of a telescopic structure, and include support leg knobs 22 for locking and releasing. The table clamp 5, the support legs 9, and the universal wheels 10 may constitute a keeping portion, which is configured to keep the traction system in a stable state during operation.

The driving mechanism is arranged on the base 14. In this embodiment, it is a manual driving mechanism, including a worm wheel 24 and a worm screw 23, where one end of the worm screw 23 is connected to a handle 26. The worm wheel 24 is connected to an output shaft 27 by a coupling, and a telescopic shaft 25 is telescopically connected to the output shaft 27, and is not rotatable relative to the output shaft 27 but can make telescopic movement along an axial direction. The telescopic shaft 25 is connected to the connecting rod 4 by a coupling 12. The handle 26 is operated to rotate the worm screw 23, and the worm wheel 24 is driven to rotate, so that the output shaft 27 rotates to drive the connecting rod 4 to rotate, so as to complete the transmission of a driving force.

Second Embodiment

Figure 4:
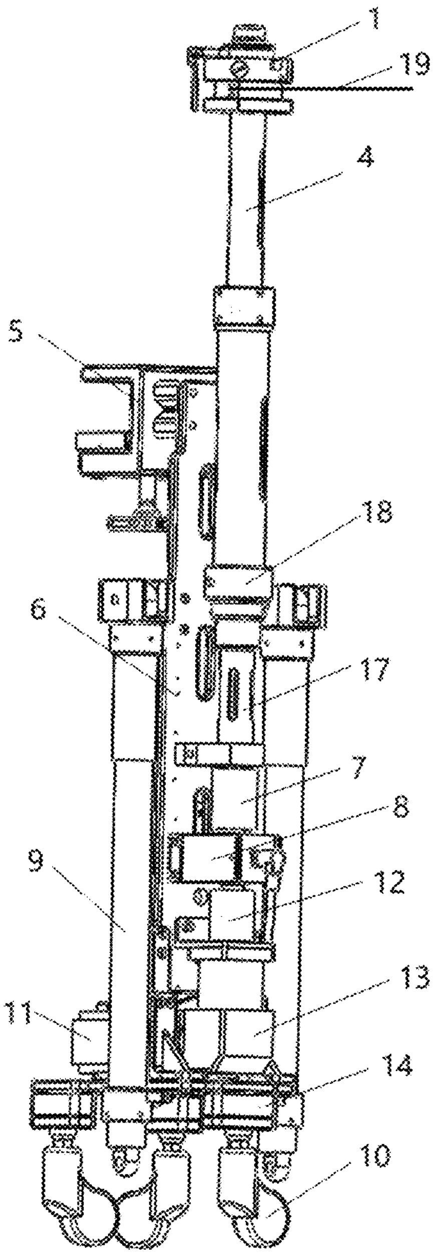
FIG. 4 is a schematic structural diagram of an electric traction system according to a second embodiment of the present disclosure.
Figure 5:
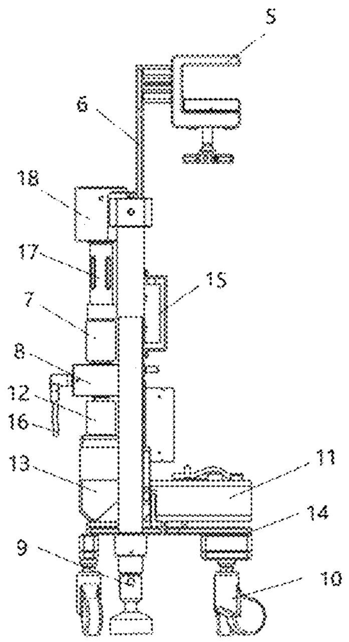
FIG. 5 is a schematic structural diagram of the electric traction system according to the second embodiment of the present disclosure.

As shown in FIGS. 4-5, an elastic traction system in this embodiment is electrically driven, and includes a connecting rod 4, where a traction wheel 1 is assembled at an upper end of the connecting rod, and a traction wire 19 is wound around the traction wheel 1. An elastic body 2 is connected to the other end of the traction wire 19. The connecting rod 4 is inserted into an annular sleeve 18. In this embodiment, the connecting rod includes two sections connected in series and inserted into each other.

A table clamp 5 is arranged at an end of a bracket 6, and the annular sleeve 18 is arranged on the bracket 6 and is lower than the table clamp 5 in position. The bracket 6 and a base 14 are vertically connected together. A motor 11 is arranged on the base 14, an output shaft of the motor 11 is connected to a speed reducer 13, an output shaft of the speed reducer 13 is vertically upward and is connected to a torsion tester 8 by a coupling 12, the other end of the torsion tester 8 is connected to one end of a transmission shaft 17 by a coupling 7, and the other end of the transmission shaft 17 is located in the annular sleeve 18 and is in clamped connection with the connecting rod 4 in the annular sleeve 18.

Three universal wheels 10 are arranged on the base 14. Two support legs 9 are arranged on two sides of the traction system, and the support legs 9 are of an electric push rod structure. A control unit 15 is arranged on the bracket 6 and is electrically connected to the torsion tester 8 by a signal line 16. The control unit 15 is electrically connected to the motor 11 and the support legs 9, respectively. According to a height of an operating table, a height of the support legs 9 can be adjusted under the control of the control unit 15, so that the table clamp 5 is clamped on a table board. In this case, the support legs 9 are supported on the ground. The table clamp 5 and the support legs 9 may constitute a keeping portion, which is configured to keep the traction system in a stable state during operation.

Figure 6:
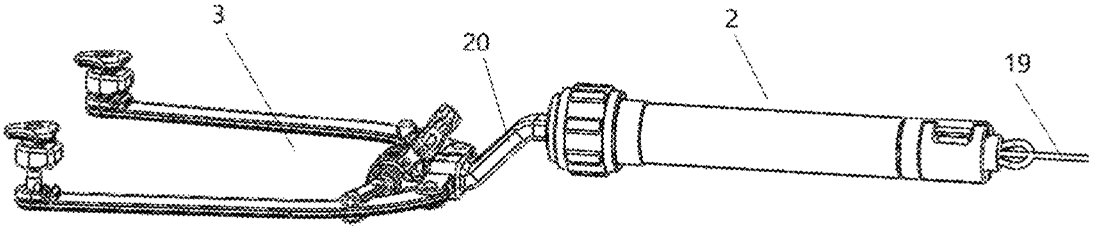
FIG. 6 is a schematic connection diagram of an electric traction bow in an embodiment of the present disclosure.

As shown in FIG. 6, a connecting arm 20 is connected to one end of an elastic traction bow 3 and is configured to be connected to the elastic body 2, and the traction wire 19 is connected to the other end of the elastic body 2 and may be connected to the traction system. The connecting arm 20 is detachably connected between the traction bow 3 and the elastic body 2. The traction bow 3 includes a ratchet wrench 300, which is configured to adjust a tension. The ratchet wrench 300 can be subjected to bidirectional adjustment, so that a magnitude of the tension is convenient to adjust.

Figure 7:
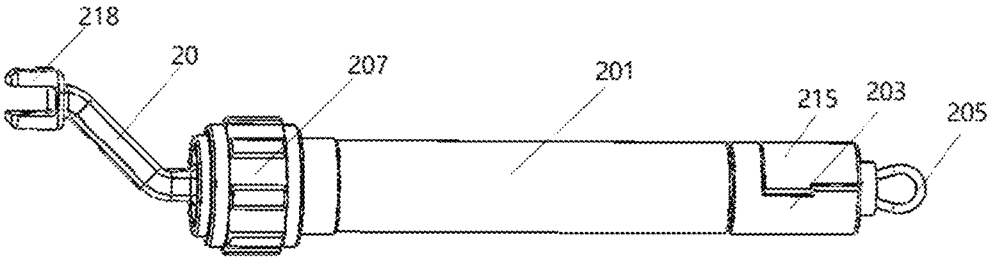
FIG. 7 is a schematic diagram of an elastic body and a connecting rod in a connection state in the embodiment of the present disclosure.

As shown in FIG. 7, the elastic body 2 includes an outer barrel 201, which is cylindrical. A moving portion 203 is arranged at one end of the outer barrel 201, and a turnover cover 215 is arranged on the moving portion 203. A connecting ring 205 is arranged at an end of the moving portion 203 and may be configured to be connected to the traction wire 19. A connecting portion is arranged at the other end of the elastic body 2, and the connecting arm 20 is inserted into the connecting portion. A locking sleeve 207 is sleeved outside the connecting portion.

Figure 8:
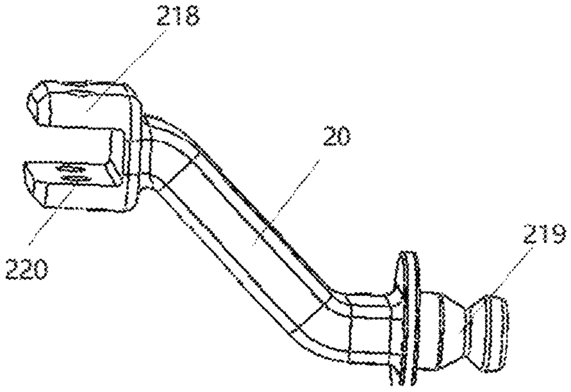
FIG. 8 is a schematic diagram of the connecting rod in the embodiment of the present disclosure.

As shown in FIG. 8, a connector 218 is arranged at one end of the connecting arm 20 and configured to be connected to the traction bow 3, and an annular clamping groove 219 is arranged at the other end of the connecting arm and configured to be connected into a connection interface of the elastic body 2. In this embodiment, the connector is of a U-shaped structure provided with connecting holes 220 on upper and lower side walls.

Figure 9:
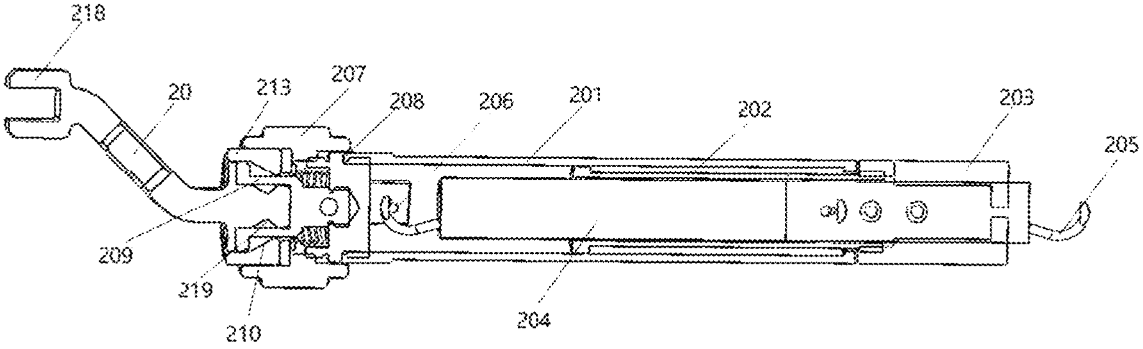
FIG. 9 is a schematic sectional view of the elastic body and the connecting rod in the embodiment of the present disclosure.
Figure 10:
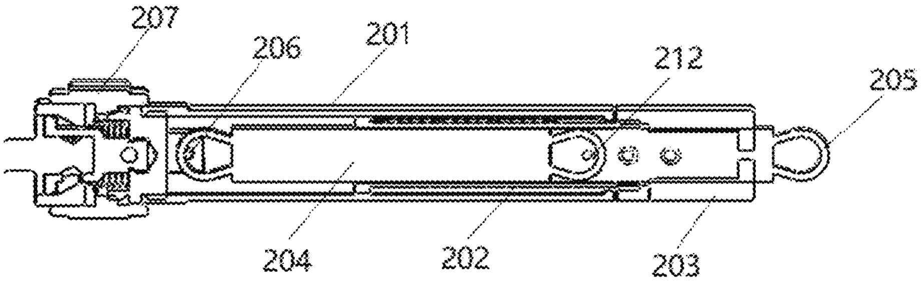
FIG. 10 is a schematic sectional view of the elastic body in the embodiment of the present disclosure.
Figure 11:
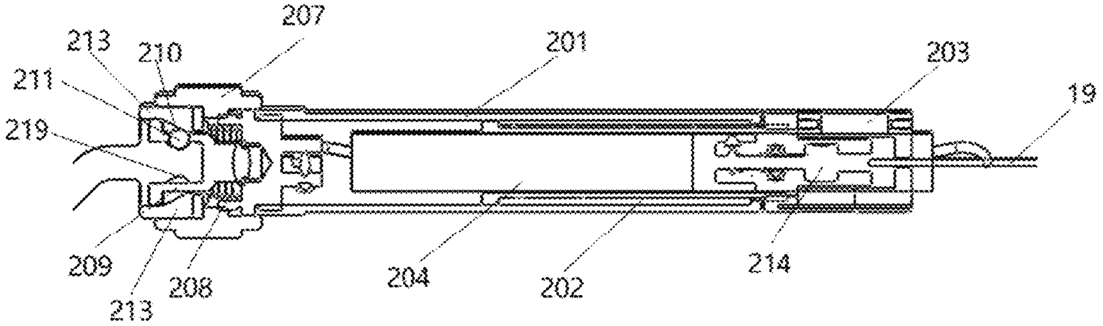
FIG. 11 is a schematic sectional view of the elastic body in the embodiment of the present disclosure.

As shown in FIG. 9-11, the elastic body 2 includes a spring 204 arranged in the outer barrel 201 and having one end fixedly connected to the connecting portion by a spring hanging point 206 and the other end fixedly connected to the moving portion 203 by a spring hanging point 212. The elastic body 2 further includes an inner barrel 202 arranged in the outer barrel 201 and having one end connected to the moving portion 203, and the spring 204 is partially arranged in the inner barrel 202.

The connecting portion of the elastic body 2 includes an interface inner barrel 209 and an interface outer barrel 213 sleeved outside the interface inner barrel 209. The interface inner barrel 209 is uniformly provided with a plurality of through holes along an outer circumference. Steel balls 211 are arranged between the interface inner barrel 209 and the interface outer barrel 213, and partially enter the through holes. When the interface outer barrel 213 slides relative to the interface inner barrel 209, the steel balls 211 can extend into the interface inner barrel 209 or exit from the interface inner barrel 209.

As shown in figure, an inner wall of the interface outer barrel 213 is provided with an inclined portion 210 and a parallel portion in natural transition connection. A rear of the interface outer barrel 213 is provided with an interface spring 208, which provides a pre-thrust for the interface outer barrel 213. When the interface outer barrel 213 is located in a locking position, the steel balls 211 are located between the through holes of the interface inner barrel 209 and the inclined portion 210 of the interface outer barrel 213, and the steel balls 211 are squeezed by the inclined portion 210 to partially extend into the interface inner barrel 209. When sliding relative to the interface inner barrel 209, the interface outer barrel 213 moves to an unlocking position against an elastic force of the interface spring 208. In this case, the inclined portion 210 of the interface outer barrel 213 does not squeeze the steel balls 211 any more. The steel balls 211 are located between the parallel portion and the through holes, and parts, extending into the interface inner barrel 209, of the steel balls 211 are retractable.

An annular clamping groove 219 is arranged at one end of the connecting rod 20. When the connecting rod 20 is inserted, the annular clamping groove 219 is inserted into the interface inner barrel 209. The annular clamping groove 219 corresponds in position to the through holes of the interface inner barrel 209. The steel balls 211 extending into the interface inner barrel 209 are clamped in the annular clamping groove 219.

The locking sleeve 207 is sleeved outside the interface outer barrel 213 and is in threaded connection with the outer barrel 201. After the connection of the connecting arm 20 is completed and the interface outer barrel 213 returns to the locking position, the locking sleeve 207 is rotated to lock the interface outer barrel 213, so as to prevent the separation of the connecting arm 20 due to sliding of the interface outer barrel 213 thanks to a misoperation.

Figure 12:
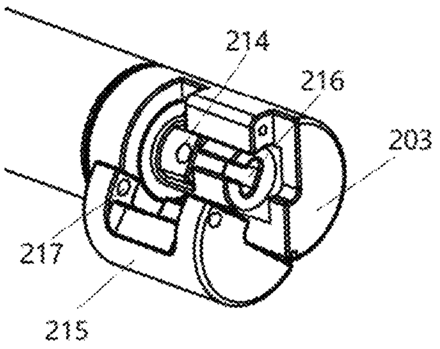
FIG. 12 is a schematic diagram of a turnover cover of a moving portion in an open state in the embodiment of the present disclosure.

As shown in FIG. 12, the moving portion 203 includes a turnover cover 215 having one end pivotally connected to the moving portion 203 and the other end openably clamped to the moving portion, where a locking hole 217 is arranged at a clamping end of the turnover cover and configured to lock the turnover cover 215. In a state where the turnover cover 215 is closed, the moving portion 203 and the turnover cover 215 have a cylindrical shape. The turnover cover 215 can be opened to expose a clamping groove 204 and a wire groove 216 arranged inside the moving portion 203, and the wire groove 216 has one end connected to the clamping groove 204 and the other end communicating with a wire hole on a surface of the moving portion 203. The clamping groove 204 is configured to be conveniently connected to the traction wire 19.

Figure 13:
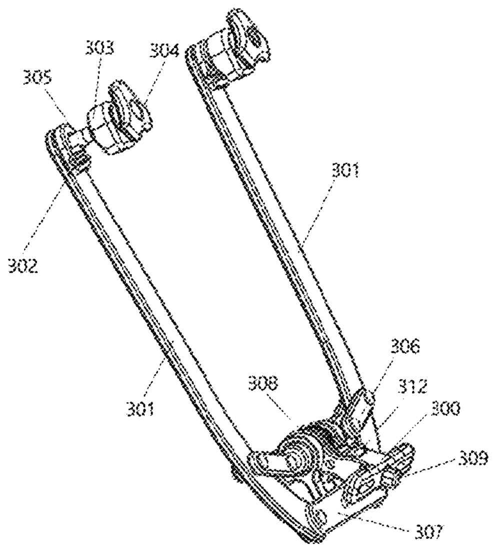
FIG. 13 is a schematic structural diagram of a tensional traction bow in the embodiment of the present disclosure.
Figure 14:
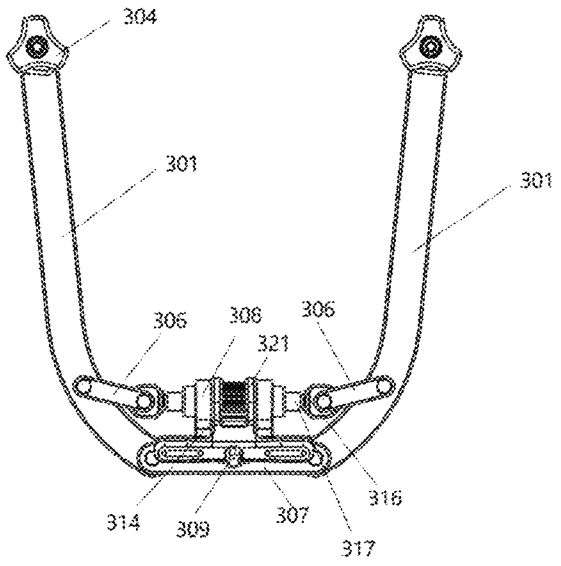
FIG. 14 is a schematic structural diagram of the tensional traction bow in the embodiment of the present disclosure.

As shown in FIGS. 13 and 14, the traction bow 3 includes a pair of bow arms 301 arranged symmetrically, where a clamp base 302 is arranged at an end of each bow arm 301. Front ends of the bow arms 301 are arc-shaped, and a connecting arm 307 is rotatably connected to the front ends of the two bow arms 301 and is connected to the connector 218 of the connecting arm 20. A pair of tension arms 306 are symmetrically arranged near the front ends of the bow arms 301, each tension arm 306 has one end rotatably connected to the corresponding bow arm 301 and the other end rotatably connected to a connecting piece 316, the connecting piece 316 has one end connected to the corresponding tension arm 306 by a rotary shaft and the other end provided with an external threaded rod, and the external threaded rods of the two connecting pieces 316 have opposite thread directions.

A ratchet shaft 317 is connected to the connecting arm 307 by a shaft sleeve 308. Internal threaded holes are arranged at two ends of the ratchet shaft 317, respectively, and the two ends of the ratchet shaft have opposite thread directions. The internal threaded holes are in threaded connection with the external threaded rods of the connecting pieces 316. Ratchet teeth 314 are arranged outside the ratchet shaft 317 and located in a middle of the ratchet shaft 317, and surround the ratchet shaft 317.

The ratchet wrench 300 is connected to the ratchet shaft 317 by two wrench shaft sleeves 321, so that the ratchet wrench 300 can rotate about the ratchet shaft 317. A pawl 312 is arranged in a middle of the ratchet wrench 300 and corresponds in position to the ratchet teeth 314.

The clamp base 302 is arranged near the end of the bow arm 301 and movably arranged on the bow arm 301. A needle groove is arranged on the clamp base 302, and lines may be arranged on a surface of the needle groove to increase a frictional force.

A clamp upper seat 303 is correspondingly arranged on the clamp base 302, a knob 304 is connected to one end of a lead screw 305, and the lead screw 305 passes through the clamp upper seat 303 and is connected to the clamp base 302. During use, a bone needle can be placed in the needle groove of the clamp base 302, and the clamp upper seat 303 can be fastened and connected to the clamp base 302 by turning the knob 304, so as to clamp the bone needle.

Figure 15:
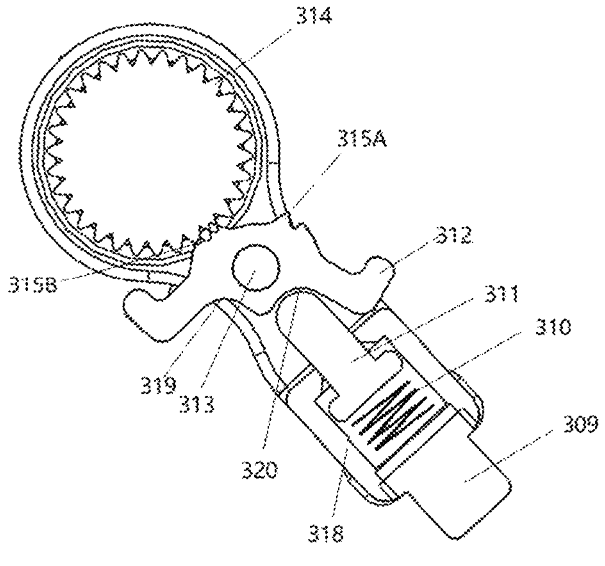
FIG. 15 is a schematic sectional view of a ratchet mechanism in the embodiment of the present disclosure.

As shown in FIG. 15, the pawl 312 includes a first pawl tooth 315A and a second pawl tooth 315B. The pawl 312 is arranged on a pawl rotating shaft 313 and can be rotated, so that the first pawl tooth 315A or the second pawl tooth 315B is engaged with the ratchet teeth 314. In this case, the pawl wrench 300 is turned, and the ratchet shaft 317 is driven by the pawl 312 to rotate. The first pawl tooth 315A and the second pawl tooth 315B are configured to implement bidirectional rotation of the ratchet shaft 137 by the ratchet wrench 300.

An ejector block 311 is configured to limit the pawl 312. The ejector block 311 is against a first position 319 or a second position 320 (two recess positions in figure) on a back of the pawl 312. When the ejector block 311 is against the first position 319, the first pawl tooth 315A is engaged with the ratchet teeth 314, and when the ejector block 311 is against the second position 320, the second pawl tooth 315B is engaged with the ratchet teeth 314.

A spring cavity 318 is arranged in a middle of the ratchet wrench 300, a spring 310 is arranged in the spring cavity 318, the ejector block 311 is located at a front end of the spring 310, a sealing cap 309 seals the spring cavity 318, and the spring 310 provides a pre-thrust for the ejector block 311. The ejector block 311 is arranged elastically, so that the ejector block can be easily switched between the first position 319 and the second position 320 by pulling the pawl 312, and then a rotation direction of the ratchet shaft 317 can be switched, so as to increase or reduce the tension.

Figure 16:
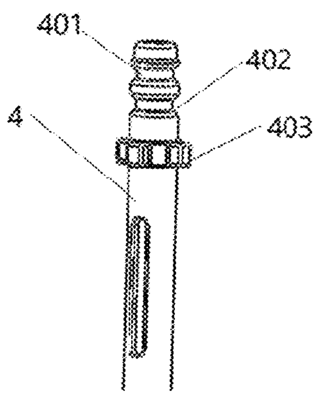
FIG. 16 is a schematic structural diagram of the connecting rod in the embodiment of the present disclosure.

As shown in FIG. 16, the connecting rod 4 is cylindrical and is matched with a through hole 101 of the traction wheel 1, and the traction wheel 1 is assembled on the connecting rod 4 via the through hole 101. A first annular groove 401, a second annular groove 402, and a cross tenon 403 are arranged at an end of the connecting rod 4 in sequence from top to bottom.

Figure 17:
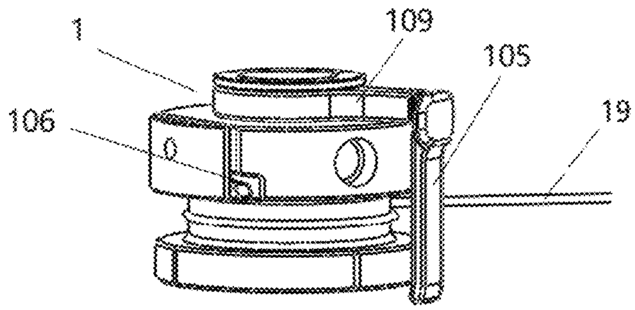
FIG. 17 is a schematic structural diagram of a traction wheel in the embodiment of the present disclosure.
Figure 18:
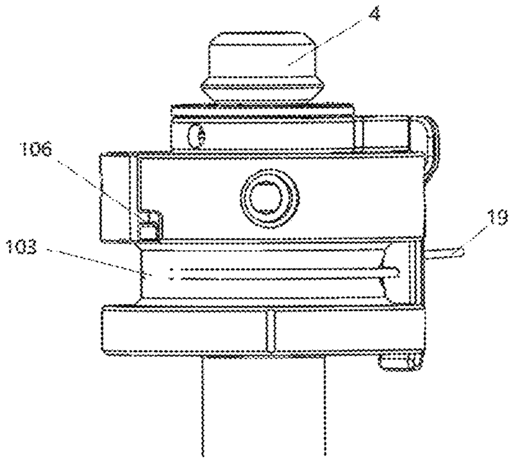
FIG. 18 is a schematic structural diagram of the traction wheel assembled on the connecting rod in the embodiment of the present disclosure.
Figure 19:
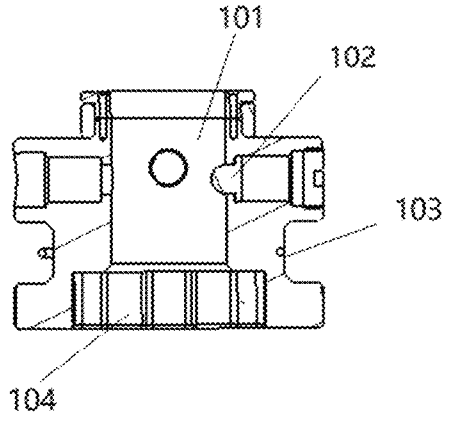
FIG. 19 is a schematic diagram of a sectional structure of the traction wheel in the embodiment of the present disclosure.

As shown in FIGS. 17-19, the traction wheel 1 includes a traction wheel body which is of a roughly cylindrical structure and has the penetrative through hole 101 in a middle. The traction wheel 1 is assembled on the connecting rod 4 via the through hole 101. A wire groove 103 is arranged on an outer circumference of the traction wheel body, and the traction wire 19 has one end fixedly connected to the wire groove 103 and is wound in the wire groove 103.

A cross clamping groove 104 is arranged at a bottom of the traction wheel body and communicates with the through hole 101. A plurality of spring cavities 108 are arranged in a middle of the traction wheel body, communicate to the through hole 101 in the middle from the traction wheel body, and are uniformly distributed around the through hole 101. Springs are mounted in the spring cavities 108, elastic joints 102 are arranged at front ends of the springs, back ends of the springs abut against sealing covers 107, and the sealing covers 107 are mounted on the traction wheel body to seal the spring cavities 108. The springs provide a pre-thrust for the elastic joints 102. Front ends of the elastic joints 102 are hemispherical and can elastically extend into the through hole 101 or retract into the spring cavities 108.

The traction wheel 1 further includes a rotating ring 109, which is arranged on an upper end surface of the traction wheel 1, coaxial with the through hole 101, and rotatable relative to the traction wheel 1. A baffle 105 is connected to the rotating ring 109 and located on an outer side of the wire groove 103.

Figure 20:
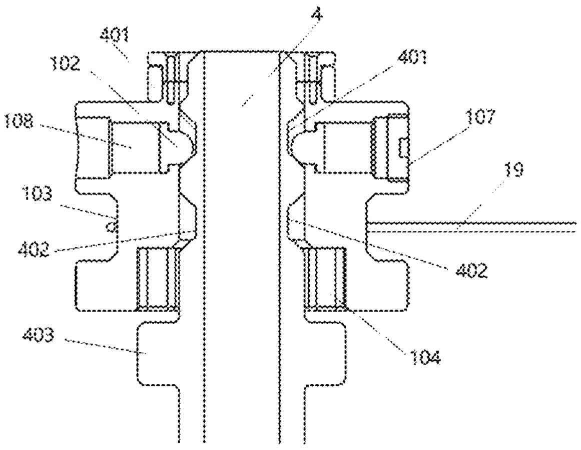
FIG. 20 is a schematic diagram of a sectional structure of the traction wheel and the connecting rod in a rotary clamping state in the embodiment of the present disclosure.
Figure 21:
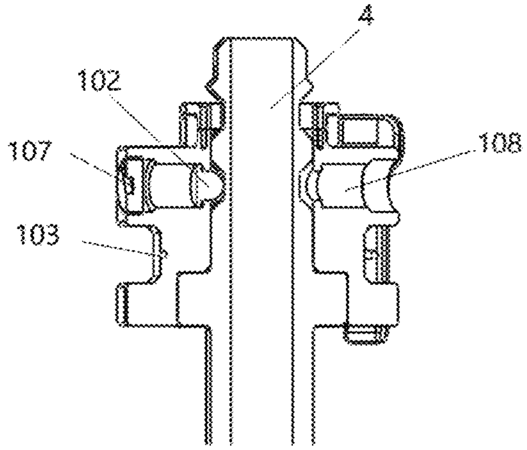
FIG. 21 is a schematic diagram of a sectional structure of the traction wheel and the connecting rod in a fixed clamping state in the embodiment of the present disclosure.

As shown in FIG. 20, the traction wheel 1 and the connecting rod 4 are in a rotary clamping state. In this case, the elastic joints 102 are clamped in the first annular groove 401 of the connecting rod 4, and the traction wheel 1 can rotate about the connecting rod 4. The traction wire 19 rotates about the connecting rod 4, which can implement the take-up and pay-off of the traction wire 19.

As shown in FIG. 8, the traction wheel 1 and the connecting rod 4 are in a fixed clamping state. In this case, the elastic joints 102 are clamped in the second annular groove 402 of the connecting rod 4. The cross clamping groove 104 of the traction wheel 1 is in clamped connection with the cross tenon 403 of the connecting rod 4, so that the traction wheel 1 cannot rotate about the connecting rod 4. In this case, the connecting rod 4 can be driven by a driving apparatus to rotate, the traction wheel 1 rotates along with the connecting rod 4, and the traction wire 19 is wound in the wire groove 103 of the traction wheel 1 and continuously tightened, so as to tension the traction bow, which implements the traction operation on a site of a patient.

Finally, it should be noted that the above embodiments are merely used to illustrate the technical solutions of the present disclosure, but not to limit them; although the present disclosure has been described in detail with reference to the above-mentioned embodiments, those of ordinary skill in the art should understand that: they may still make modifications to the technical solutions described in the above-mentioned embodiments, or make equivalent substitutions to some of the technical features; and these modifications or substitutions do not make the essence of the corresponding technical solutions depart from the spirit and scope of the technical solutions of the embodiments of the present disclosure.

The invention claimed is:

1. An elastic traction system, comprising:

a driving mechanism, configured to provide traction power;

a connecting rod, connected to an output shaft of the driving mechanism and rotating along with the output shaft;

a traction wheel, arranged at an end of the connecting rod and capable of rotating along with the connecting rod, where a traction wire is connected to the traction wheel; and an elastic traction bow, connected to the traction wire; wherein the traction wheel comprises:

a traction wheel body, having a penetrative circular through hole in a middle;

a wire groove, arranged on an outer circumference of the traction wheel body:

a rotary clamping portion, configured to rotatably clamp the traction wheel to the connecting rod; and a fixed clamping portion, configured to non-rotatably clamp the traction wheel to the connecting rod;

the rotary clamping portion comprises a plurality of elastic joints uniformly distributed around the circular through hole, and the elastic joints are capable of retractably extending into the circular through hole.

2. The elastic traction system according to claim 1, wherein the elastic traction bow comprises:

an elastic body, having one end connected to the traction wire; and a tensional traction bow, having one end connected to the other end of the elastic body.

3. The elastic traction system according to claim 2, wherein the elastic body comprises an outer barrel and an elastic element, wherein a moving portion is arranged at one end of the outer barrel and connected to the traction wire, a connecting portion is arranged at the other end of the outer barrel, and the tensional traction bow is connected to the connecting portion; and the elastic element is arranged in the outer barrel and has one end fixedly connected to the connecting portion and the other end fixedly connected to the moving portion.

4. The elastic traction system according to claim 2, wherein the tensional traction bow comprises:

a pair of bow arms arranged symmetrically, wherein a connecting portion connected to a bone needle is arranged at an end of each of the bow arms;

a connecting arm, rotatably connected to a front end of each of the bow arms;

a pair of tension arms, symmetrically arranged at positions, close to the front ends, of the bow arms, wherein one end of each of the tension arms is rotatably connected to a corresponding bow arm; and an adjustment mechanism, having two ends movably connected to the other ends of the pair of tension arms, respectively, and configured to adjust the pair of tension arms to move close to or away from each other.

5. The elastic traction system according to claim 1, wherein the rotary clamping portion comprises:

a plurality of spring cavities, uniformly distributed around the circular through hole and penetrating through the traction wheel body to communicate with the circular through hole;

a plurality of springs, arranged in the plurality of spring cavities, respectively;

the plurality of elastic joints arranged in the plurality of spring cavities, respectively, wherein each of the elastic joints has one end extending into the circular through hole and the other end abutting against a corresponding one of the springs; and a plurality of sealing covers, arranged on the traction wheel body and configured to seal the spring cavities.

6. The elastic traction system according to claim 1, wherein the driving mechanism comprises a motor and a speed reducer, and the output shaft is connected to the connecting rod by the speed reducer.

7. The elastic traction system according to claim 6, further comprising a control unit and a torsion tester, wherein the torsion tester is connected between the speed reducer and the connecting rod by a coupling, and the control unit is electrically connected to the torsion tester and the motor.

8. The elastic traction system according to claim 1, wherein the driving mechanism comprises a worm wheel and a worm screw matched with each other, one end of the worm screw is connected to a handle, and a shaft center of the worm wheel is connected to the output shaft.

* * * * *